US00PP33394P2

(12) United States Plant Patent
Van Swieten

(10) Patent No.: US PP33,394 P2
(45) Date of Patent: Aug. 24, 2021

(54) ***PHALAENOPSIS* ORCHID PLANT NAMED 'PHALHOKCO'**

(50) Latin Name: ***Phalaenopsis* hybrid**
Varietal Denomination: PHALHOKCO

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,111

(22) Filed: Mar. 10, 2021

(51) Int. Cl.
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

UPOV hit on *Phalaenopsis* plant named, 'PHALHOKCO', QZ PBR 2019/2065, filed Aug. 30, 2019.*

* cited by examiner

*Primary Examiner* — Anne Marie Grunberg
(74) *Attorney, Agent, or Firm* — Jondle & Associates, P.C.

(57) ABSTRACT

A new and distinct variety of *Phalaenopsis* plant named 'PHALHOKCO', particularly characterized by light reddish-purple flowers with light red-purple lips, a flat flower shape in lateral view, a concave lateral sepal shape in cross section, and is propagated by meristem tissue culture, is disclosed.

3 Drawing Sheets

Genus and species: *Phalaenopsis* hybrid.
Variety denomination: 'PHALHOKCO'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALHOKCO'.

The new *Phalaenopsis* plant is a product of a planned breeding program conducted by the inventor in Bleiswijk, the Netherlands. The objective of this breeding program was to create a new *Phalaenopsis* plant with light reddish-purple flowers with light red-purple lips, suitable for potted plant production.

The new *Phalaenopsis* plant 'PHALHOKCO' is a result of cross-pollination made by the inventor in August 2010 in Bleiswijk, the Netherlands, of the proprietary female, or seed parent, *Phalaenopsis* hybrid 'PHALOFMO' (U.S. Plant Pat. No. 28,736) with the proprietary male, or pollen parent, *Phalaenopsis* hybrid '28634-03' (unpatented).

The new *Phalaenopsis* was selected by the inventor as a single plant within the progeny of the stated cross-pollination in a controlled greenhouse in Bleiswijk, the Netherlands, in July 2013. Asexual reproduction of the new *Phalaenopsis* plant by meristem tissue culture since 2014 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Aug. 30, 2019

(Application no. 2019/2065), by Applicant who obtained the subject matter disclosed directly from the inventor. 'PHALHOKCO' has not been made publicly available or sold anywhere in the world prior to the effective filing date of this application with the exception of sales or disclosures made one year or less before the effective filing date of this claimed invention by Applicant who obtained 'PHALHOKCO' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALHOKCO' as a new and distinct variety of *Phalaenopsis* plant:

1) Light reddish-purple flowers with light red-purple lips;
2) Flower shape in lateral view is flat; and
3) Lateral sepal shape in cross section is concave.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in January 2021. Colors in the photographs may differ from the color values cited in the detailed botanical description, which accurately describe the actual colors of the new variety.

DESCRIPTION OF THE NEW VARIETY

Figure 1:
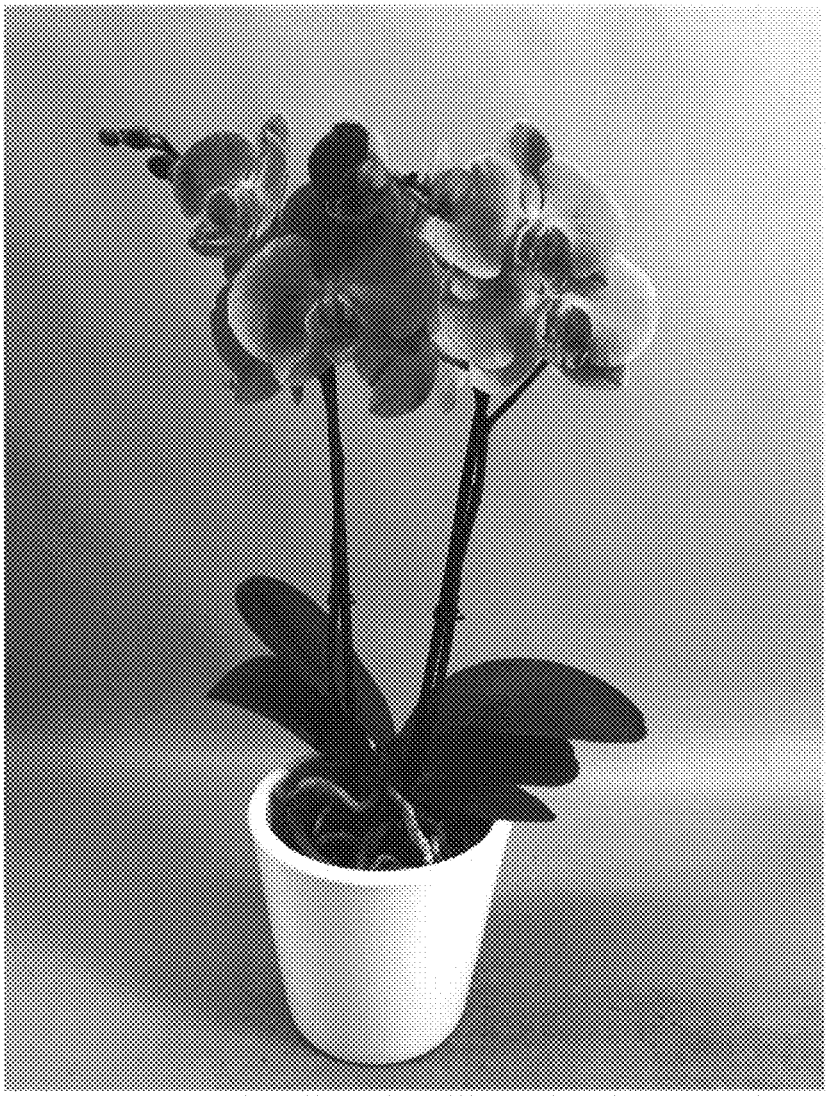
FIG. 1 shows the overall plant habit, including blooms, buds, and foliage of 'PHALHOKCO'.
Figure 2:
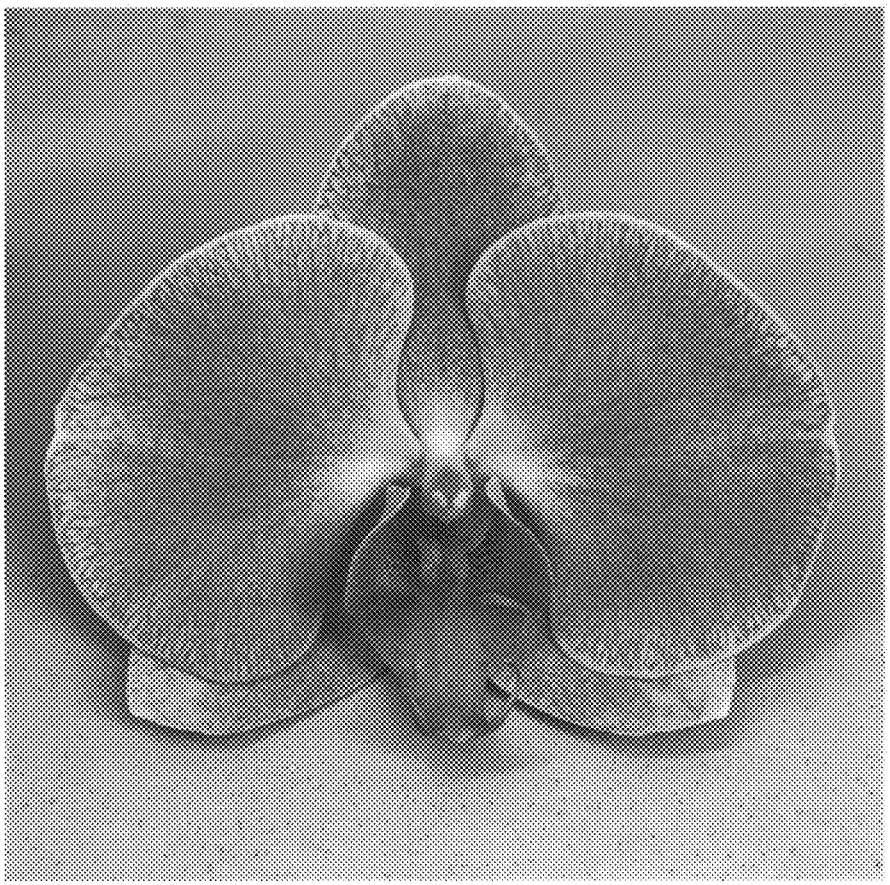
FIG. 2 shows a close-up of a flower of 'PHALHOKCO'.
Figure 3:
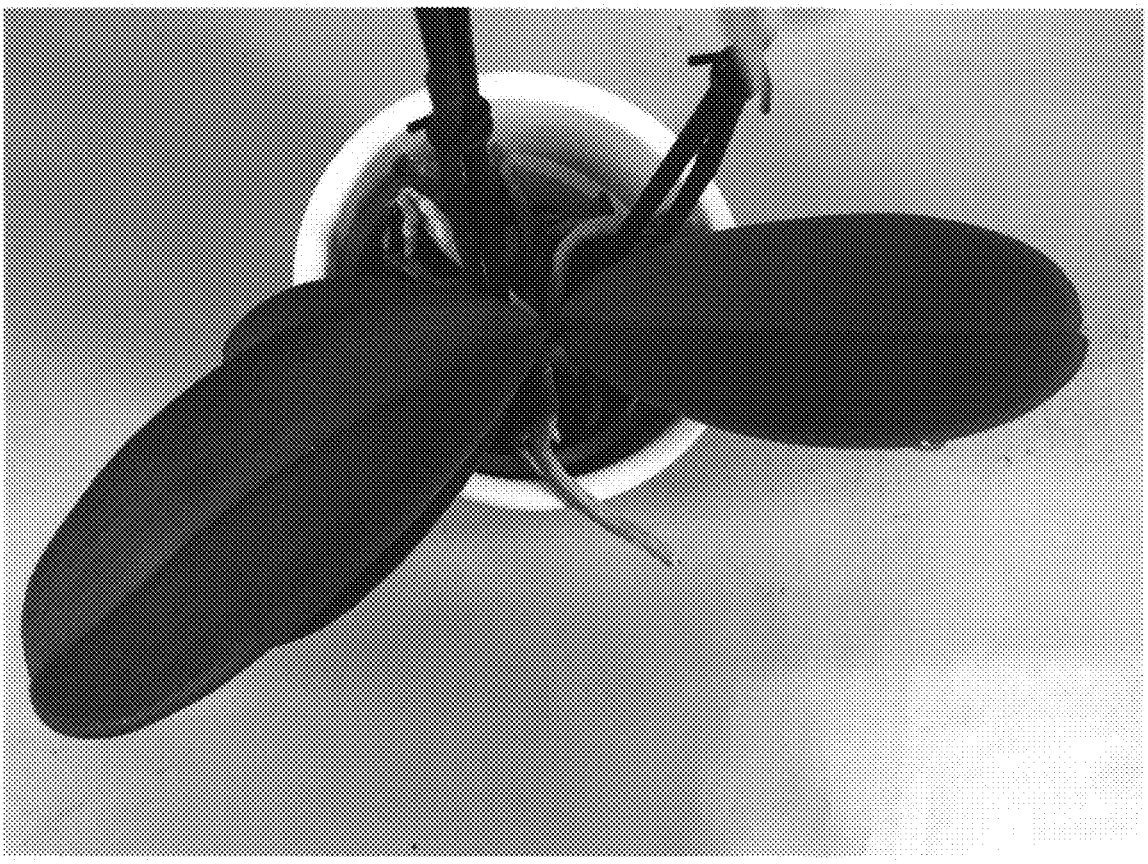
FIG. 3 shows an overhead view of the leaves of 'PHALHOKCO'.

The following detailed description sets forth the distinctive characteristics of 'PHALHOKCO'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in January 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALHOKCO'.

Parentage:

*Female parent*.—*Phalaenopsis* cultivar 'PHALOFMO' (U.S. Plant Pat. No. 28,736).

*Male parent*.—*Phalaenopsis* cultivar '28634-03' (unpatented).

Propagation:

*Type*.—Meristem tissue culture.

Roots:

*Root description*.—Greyed-green (a color in between RHS 190B and RHS 190C) colored roots with branching lateral roots having yellow-green (RHS 144C) with a hint of light reddish-purple (RHS N78D) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme and panicle inflorescence.

*Height* (*from soil level to top of inflorescence*).—Approximately 35.0 cm to 40.0 cm.

*Width* (*measured from leaf tips*).—About 28.0 cm to 30.0 cm.

*Vigor*.—Strong.

Leaves:

*Mature leaves*.—Quantity per plant: 6 to 7 leaves are produced before flowering. Length (fully expanded): 15.0 cm to 18.0 cm. Width: 6.5 cm to 7.5 cm. Position of the broadest part of the leaf: Toward apex. Shape: Obovate. Base shape: Moderately elongated. Apex: Obtuse to rounded unequal. Leaf blade angle with the petiole (measured from the horizontal position): Between 15 degrees and 35 degrees. Leaf margin: Entire. Color: Upper surface: RHS 146A. Lower surface: RHS 146B with reddish-brown margin (RHS 200B) toward the tip. Texture (both upper and lower surfaces): Smooth. Thickness: 2.0 mm to 3.0 mm. Variegation: Absent. Venation: Pattern: Parallel. Color of the midvein: Upper surface: RHS 146A. Lower surface: RHS 146B.

Peduncle:

*Quantity per plant*.—1 to 2.

*Number of flowers per peduncle*.—8 to 12.

*Length*.—35.0 cm to 40.0 cm.

*Diameter*.—4.0 mm to 5.0 mm.

*Strength*.—Strong.

*Aspect*.—Upright to slightly pendent.

*Texture*.—Smooth.

*Color*.—Reddish-brown (a color in between RHS 187B and RHS 200B) with a touch of light yellow-green (RHS 145D).

*Internode length*.—3.0 cm to 4.0 cm.

Inflorescence description:

*Appearance*.—Upright to slightly pendent, raceme and panicle inflorescence with bilaterally symmetrical flowers that open in succession beginning with the lowermost flower.

*Number of inflorescences*.—1 to 2.

*Inflorescence size*.—Height (from base to tip): 130.0 mm to 170.0 mm.

*Flowering time*.—First flowers can be expected 10 to 11 months after planting in a 12-cm pot.

*Flower*.—Height: 90.0 mm to 95.0 mm. Diameter: 100.0 mm to 105.0 mm. Depth of lip: 26.0 mm to 28.0 mm.

*Flower longevity*.—On the plant: 16 to 19 weeks.

*Flower shape*.—Flat.

*Fragrance*.—Absent.

*Flower bud*.—Average size: Large. Length: 24.0 mm to 26.0 mm. Width: 19.0 mm to 21.0 mm. Shape: Egg shaped. Color: Hint of yellow-green (RHS 145C) at the base; purplish-red (RHS N77B) toward the tip.

*Petals*.—Arrangement: Open/free. Shape: Semi-circular. Apex: Emarginated asymmetric. Margin: Weakly undulated. Length (from base to tip): 47.0 mm to 49.0 mm. Width: 65.0 mm to 67.0 mm. Position of the broadest part of the petal: Toward the base. Color (when fully opened): Upper surface: Basic color: Light reddish-purple (a color in between RHS N78C and RHS N78D). Over color: Touch of white (RHS NN155C) at the base; reddish-purple shade and stripes (RHS N78B). Lower surface: Basic color: Light reddish-purple (RHS N78D). Over color: Hint of reddish-purple (RHS N78B) at the base; light purple (RHS 76A) at the middle and stripes (a color in between RHS N78B and RHS N78C) toward margin. Number of spots and stripes on the petals (upper surface): Many stripes. Color of spots and stripes on the petals (upper surface): A color in between RHS N78B and RHS N78C. Density of netting of the petals (upper surface): None. Color of the netting (upper surface): Not applicable.

*Dorsal sepal*.—Shape: Elliptic. Apex: Obtuse symmetric. Margin: Entire. Length (from base to tip): 51.0 mm to 53.0 mm. Width: 37.0 mm to 39.0 mm. Position of the broadest part of the dorsal sepal: At the middle. Color (when fully opened): Upper surface: Basic color: Purplish-pink (RHS N78C). Over color: Reddish-purple shade (RHS N78B); light purple edge (RHS 76A); reddish-purple stripes and netting (RHS N78B). Lower surface: Basic color: Light reddish-purple (RHS N78D). Over color: Light yellow-green (RHS 145C); stripes and netting (a color in between RHS N78B and RHS N78C). Number of spots and stripes on the dorsal sepals (upper surface): Few diluting stripes. Color of spots and stripes on the dorsal sepals (upper surface): RHS N78B. Density of netting of the dorsal sepals (upper surface): Low. Color of the netting (upper surface): RHS N78B.

*Lateral sepals*.—Shape: Ovate. Apex: Obtuse symmetric. Margin: Entire. Length (from base to tip): 50.0 mm to 52.0 mm. Width: 30.0 mm to 32.0 mm. Position of the broadest part of the lateral sepal: At the base. Color (when fully opened): Upper surface: Basic color: Light reddish-purple (RHS N78D). Over color: Light yellow-green (RHS 145D) at the base; purplish-pink stripes and netting (RHS N78C) toward margin. Lower surface: Basic color: Purplish-pink (RHS N78C). Over color: Hint of light yellow-green (RHS 145D) at the base; reddish-purple stripes (RHS N78B). Number of spots and stripes on the lateral sepals (upper surface): Few diluting stripes. Color of spots and stripes on the lateral sepals (upper surface): RHS N78C. Density of netting of the lateral sepals (upper surface): Low. Color of the netting (upper surface): RHS N78C.

*Labellum* (*lip*).—Whiskers: Present. Length of whiskers: 15.0 mm to 17.0 mm. Color of whiskers: Reddish-purple (RHS N78A) with light reddish-purple margin (RHS N78D) and small white tips (RHS NN155C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Entire. Length: 20.0 mm to 24.0 mm. Width: 16.0 mm to 18.0 mm. Color: Upper surface: Purplish-red stripes (RHS 59B) at the base; dark reddish-orange (RHS 175B) at the base toward margin on one side; purplish-red stripes (RHS N78B) and light reddish-purple (RHS N78D) toward the tip. Lower surface: Touch of greenish-white (RHS 155C) at the base; dark reddish-orange (RHS 175C) toward margin on one side; reddish-purple stripes (RHS N78B) and purplish-pink (RHS N78C) toward the tip. Number of spots and stripes on the lateral lobe: Many stripes. Color of spots and stripes on the lateral lobe: RHS 59B at the base and RHS N78B toward the margin. Density of netting of the lateral lobe: None. Color of the netting: Not applicable.

*Apical lobe*.—Shape: Triangular. Margin: Entire. Length: 23.0 mm to 25.0 mm. Width: 22.0 mm to 24.0 mm. Color: Upper surface: Dark reddish-orange (RHS 175B) and touch of yellow (RHS 12A) at the base; light reddish-purple (RHS N78D) toward whiskers with reddish-purple stripes (RHS N78B) toward margin and whiskers. Lower surface: Dark reddish-orange wings (a color in between RHS 175B and RHS 175C); light purple (RHS 76A) at the middle from base toward whiskers; purplish-pink margin (RHS N78C) and diluting reddish-purple stripes (RHS N78B). Number of spots and stripes on the apical lobe: Few stripes. Color of spots and stripes on the apical lobe: RHS N78B. Density of netting of the apical lobe: None. Color of the netting: Not applicable.

*Callus*.—Average size: Medium to large. Height: 8.0 mm to 9.0 mm. Length: 6.0 mm to 7.0 mm. Width: 4.0 mm to 5.0 mm. Color: Yellow tips (RHS 12A); light yellow (RHS 12D) on sides; dotted (RHS 59B).

Reproductive organs:

*Column*.—Length: 10.0 mm to 12.0 mm. Diameter: 5.6 mm to 6.1 mm. Color: Light purple (RHS 76A) with reddish-purple tip (RHS N78B).

*Pollinia*.—Quantity: 2. Diameter: 1.0 mm to 1.2 mm. Color: Orange (RHS 24A).

*Ovary*.—Length: 13.0 mm to 15.0 mm. Diameter: 2.5 mm to 2.8 mm.

*Pedicel*.—Length: 38.0 mm to 40.0 mm. Diameter: 3.0 mm to 3.4 mm. Color: Yellow-green (RHS 146D) with a touch of purplish-red (RHS N77B) at the base; light yellow-green (a color in between RHS 147C and RHS 145D); light purple (RHS 75B) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALHOKCO' differs from the female parent plant 'PHALOFMO' (U.S. Plant Pat. No. 28,736) in that 'PHALHOKCO' has emarginated petal apexes, whereas 'PHALOFMO' has rounded petal apexes. Additionally, 'PHALHOKCO' has narrower leaves than 'PHALOFMO'.

'PHALHOKCO' differs from the male parent plant '28634-03' (unpatented) in that 'PHALHOKCO' has reddish-purple whiskers with light reddish-purple margins and small white tips, whereas '28634-03' has white whiskers.

'PHALHOKCO' is most similar to the commercial *Phalaenopsis* plants named 'PHALFEWYP' (U.S. Plant Pat. No. 31,514) and 'PHALGUIQDI' (U.S. Plant Pat. No. 32,207). 'PHALHOKCO' differs from the commercial variety 'PHALFEWYP' in that 'PHALHOKCO' has reddish-purple whiskers with light reddish-purple margins and small white tips, whereas 'PHALFEWYP' has purplish-red whiskers. Additionally, 'PHALHOKCO' has a shorter plant height than 'PHALFEWYP'.

'PHALHOKCO' differs from the commercial variety 'PHALGUIQDI' in that 'PHALHOKCO' has light purple columns with reddish-purple tips and reddish-purple whiskers with light reddish-purple margins and small white tips, whereas 'PHALGUIQDI' has reddish-purple columns and dark purplish-red whiskers with dark red tips. Additionally, 'PHALHOKCO' has a shorter plant height than 'PHALGUIQDI'.

I claim:

1. A new and distinct variety of *Phalaenopsis* plant named 'PHALHOKCO', substantially as described and illustrated herein.

* * * * *